United States Patent [19]

Lemelson

[11] 4,299,233

[45] Nov. 10, 1981

[54] PATIENT MONITORING DEVICE AND METHOD

[76] Inventor: Jerome H. Lemelson, 85 Rector St., Metuchen, N.J. 08840

[21] Appl. No.: 81,276

[22] Filed: Oct. 3, 1979

[51] Int. Cl.³ .............................................. A61B 5/02
[52] U.S. Cl. ................................................... 128/687
[58] Field of Search ............... 128/660, 663, 671, 687, 128/689, 694, 701, 715, 721, 722, 782

[56] References Cited

U.S. PATENT DOCUMENTS

| | | | |
|---|---|---|---|
| 3,727,606 | 4/1973 | Sielaff | 128/722 |
| 3,990,296 | 11/1976 | Erikson | 128/660 |
| 4,066,072 | 1/1978 | Cummins | 128/671 |

*Primary Examiner*—William E. Kamm

[57] ABSTRACT

A cushioning device on which a human body may lie or recline, as in resting, sleeping or sitting, which cushioning device contains a transducer or pickup for body vibrations such as heart pulses, respiration or body tremors. In one form, the cushioning device is in the form of an elongated mattress, at least a portion of the upper wall of which is formed of a flexible material such as flexible plastic or resin impregnated and coated cloth. The interior of the mattress is filled with a liquid such as water or oil through which medium body vibrations may be transmitted. A transducer, such as a piezoelectric sensor or other form of sensor which is operable to sense sounds transmitted through the liquid and generate or modulate electrical signals, is operatively coupled to the liquid within the mattress either by direct contact therewith or through a flexible portion of the wall of the mattress. Electronic analyzing and display means is provided which is connected to the transducer and is either supported by the mattress or is remote therefrom. Communication between such electronic circuit analyzing means and the transducer is effected either by flexible cable or short wave communication.

10 Claims, 4 Drawing Figures

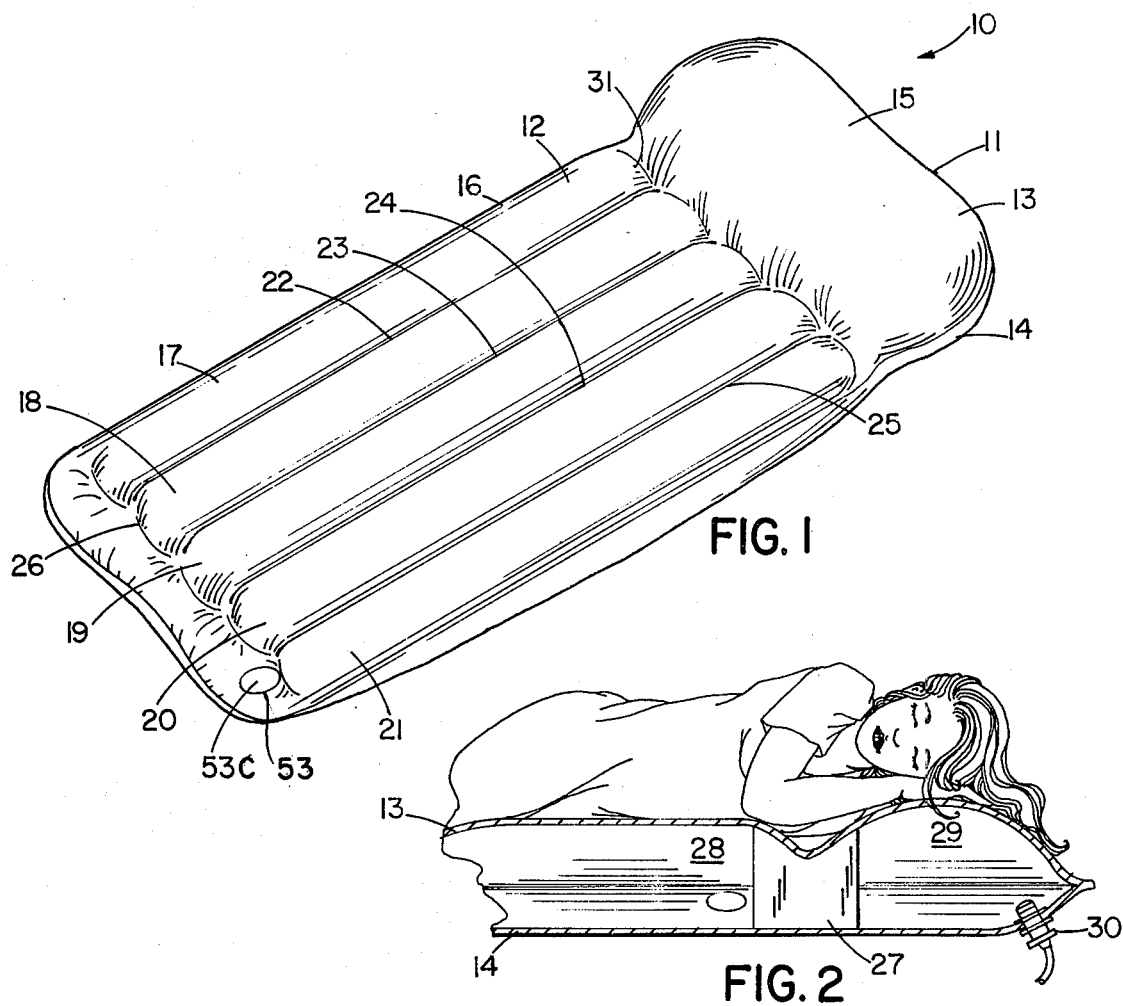
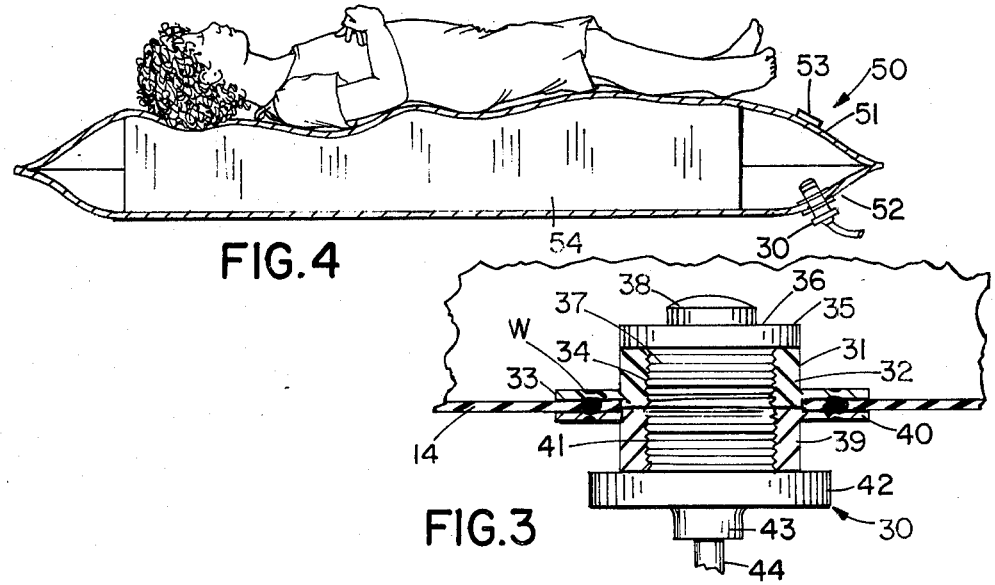

PATIENT MONITORING DEVICE AND METHOD

SUMMARY OF THE INVENTION

This invention relates to an apparatus and method for analyzing body vibrations, such as heart beat, pulse rate, respiration rate and other body vibrations or tremors, so as to provide information for local or remote monitoring, and in certain instances, for controlling medical devices for administering first aid, alleviating the condition, reducing pain or other purpose. In particular, the invention is concerned with a patient monitoring apparatus which includes a pad or mattress which is either partly or completely fabricated of a flexible sheet material and which has a flexible upper wall against which a portion of the body of a patient may recline or sit. Such pad or mattress is filled with a liquid, such as water or oil, which serves both to cushion the body resting thereon and as a transmission medium for body vibrations and sounds to be detected by one or more sound-to-electrical transducers supported within the envelope defining the mattress or cushion.

In monitoring the condition of persons who are sick or injured, it is frequently desirable to automatically determine and monitor such physiological parameters as heart beat, pulse rate, respiration and other body tremors. It is known in the art to indicate pulse rate by means of a transducer which is strapped against or taped to a portion of the body of a patient. However, the use of such a transducer has certain shortcomings including its inconvenience to the patient, the fact that it may be torn off or removed during use and the need to communicate by wire between the transducer and a remote indicator.

The instant invention provides a convenient and suitable means for indicating body vabrations including heart beat and pulse rate by permitting such vibrations to be transmitted from the body through a fluid medium to which medium a transducer is coupled in such a manner as to eliminate the need for contacting or securing a pickup to a portion of the body of the patient being monitored.

In a preferred form of the instant invention, the fluid medium is contained within a flexible mattress and serves also to cushion the body of the patient by supporting a flexible wall of the mattress. A sound-to-electrical transducer is supported either within the fluid medium or is coupled thereto through the wall of the mattress, preferably on the lower side thereof so as to be completely out of the way of the transducer and are insulated flexible cable transmits energizing current to the transducer and contains a line for receiving electrical signals which are modulated when the transducer picks up sounds and vibrational energy from the liquid.

Accordingly it is a primary object of this invention to provide a new and improved apparatus and method for detecting body vibrations such as heart beat, respiration and body tremors of persons requiring the automatic monitoring and indication of such variables.

Another object is to provide a human body vibration monitoring system employing the liquid filled cushion or mattress on which a patient may rest and sleep, the liquid of which serves both as a transmission medium for body vibrations and as a cushioning medium for the person being monitored.

Another object is to provide a monitoring system for detecting heart beat, respiration and body tremors of a patient, which system does not require direct contact of the body of a patient being monitored with the detector.

Another object is to provide an electronic system for detecting body vibrations wherein a patient being monitored is completely free of encumbering devices.

Another object is to provide a method of detecting pulse rate without the need for attaching a cuff or band to the body of a patient.

Another object is to provide a patient monitoring system which includes a transducer supporting mattress on which the patient may recline, rest or sleep which mattress is simple in structure, easy to fabricate and relatively low in cost.

Another object is to provide a new and improved structure in a body supporting mattress which may be filled with a liquid for coupling a transducer, which is secured to the mattress to the body of a person lying on the mattress, wherein such coupling is effected along the length of the mattress.

Another object is to provide a patient monitoring system and device for receiving body vibrations including heart beat and converting same to electrical signals which may be automatically analyzed to continuously determine the patient's condition without the need to connect wires or sensing devices to the body of the patient.

Another object is to provide an improved method for detecting body vibrations of a patient, such as heart beat and respiration without connecting transducers to the body of the patient and without the need to connect wires to the patient.

Another object is to provide a patient monitoring device which is simple in structure, light in weight and easily carried or stored.

With the above and such other objects in view as may hereafter more fully appear, the invention consists of the novel constructions, combinations and arrangements of parts as will be more fully described and illustrated in the accompanying drawings but it is to be understood that changes, variations and modifications may be resorted to which fall within the scope of the invention as claimed.

In the drawings:

FIG. 1 is an isometric view of a liquid filled inflatable mattress containing a patient monitoring transducer.

FIG. 2 is a partial side view of the mattress of FIG. 1 shown in cross section with a patient restng thereon.

FIG. 3 is a cross sectional view of a portion of the mattress of FIGS. 1 and 2 showing details of a transducer pick-up assembly therewith.

FIG. 4 is a side view in cross section of a modified form of patient monitoring mattress with a patient resting thereon and a pick-up transducer secured to one end of the mattress.

While the several embodiments of the instant invention which are illustrated in the drawings define elongated mattress structures on which patients or persons to be monitored for heart beat, heart rate and respiration rate are in the form of elongated inflatable mats or mattresses which are totally formed of flexible plastic sheeting such as plasticized polyvinyl chloride having a thickness in the range of about 0.008" to 0.020", such illustrated structures may be modified to include mattresses made completely of laminations of plastic and cloth or netting, plastic coated and impregnated cloth and plastic net reinforced plastic sheeting which is extrusion formed. The elongated shapes illustrated may be replaced by any suitable configuration such as pillow-lie configurations on which a patient may sit or rectangular configuration large enough to be placed on a surface or bed which is substantially wider than those illustrated. Circular or otherwise shaped mattresses may also be employed for the purposes described.

The all flexible wall mattress structures shown in the drawings may also be replaced by box-like rigid walled containers having top walls or top wall portions made of such flexible material against which flexible material a person may recline or at least partially rest in a manner such that heart beat and other body sounds will be transferred therethrough to a liquid filling the container and in contact with the flexible wall.

In FIG. 1 is shown a mattress or bed assembly 10 which is formed of a flexible, slab-like envelope 11 having a main body portion 12 and a head portion 15 defining a flexible slab-like assembly formed of at least two sheets 13 and 14 of flexible material, such as polypropylene, polyethylene, plasticized polyvinyl chloride resin, or a resin coated cloth-like material such as coated Nylon cloth webbing.

The envelope 11 is formed with a circumscribing seal line 16 defining the border of the envelope and a plurality of seals interior thereof including parallel line seals 22, 23, 24 and 25 which define respective tubular rib-like formations 17 extending most of the length of the mattress or bed. The formations 17 are also defined by respective sealing lines 26 and 31 formed within the circumscribing seal line 16 which join the side walls 13 and 14 together.

The seals or weld lines 22–25 terminate between the end portion 15 and the main body of the mattress while welding line or lines 31 join the top and bottom walls 13 and 14 to respective gussets 27 formed of strips of flexible plastic so that the volumes 28 defined by the cylindrical formations 17–21 extend to and communicate with the common interior volume 29 defining the interior of the pillow portion 15 of the mattress. While the sealing lines 26 may close off the far end of the tubular formations 17, they preferably extend only partially across the tubular formations to permit the far end of the mattress to be used for filling purposes through a fitting 53 which is sealed across an opening in the top wall 13 and contains a closure 53C.

As shown in FIG. 2, the bottom wall 14 has an opening in the end portion 15 of the envelope and sealed across such opening is the head end of a transducer assembly 30 which is operable to sense body vibrations transmitted through a liquid filling the interior volume of the enclosure and to modulate or generate an electrical signal or signals, the variations of which define such body vibrations as generated by heart beats, respiration and body tremors.

Further details of the transducer assembly 30 are illustrated in FIG. 3. Such assembly is formed to two flanged cylindrical fittings 31 and 39, preferably formed of a heat sealable plastic, the flange portions 33 and 40 of which are assembled in alignment with each other and contain respective circular seals or weld lines W joining such flanges to the bottom wall 14 of the enclosure 11. The bore defined by threaded passageways 34 and 41 extending through the centers of the cylindrical portions of the fittings 39 and 40, is shown retaining a cylindrical housing 37 containing a portion of the cylindrical side wall of the transducer housing 38 which extends to a flange base 42 having a central retaining portion 43 for a cable 44 through which suitable electrical energy is conducted from remote instrumentation, defining electrical signals representative of sounds generated by the body of a person resting on top of the mattress, as shown in the drawings, such as heart beat, respiration and other sounds.

Sealing the interior of the fittings 31 and 39 to prevent leakage of liquid from the interior of the enclosure 11 therethrough, is effected by means of a disc shaped flange 35 against the front face 36 of which is formed or mounted the end of the transducer housing 38.

In FIG. 4, a mattress assembly 50 defines a slab-like enclosure formed of flexible upper and lower wall portions 51 and 52 of the material described. A filling fitting 53 is sealed across an opening to the upper wall 51 at one end of the mattress while the flanges of an assembly 30 of the type described, including a transducer for sensing sounds generated in the liquid filling the interior volume of the mattress, is sealingly secured across an opening in the bottom wall 52 of the mattress. A plurality of elongated gussets 54 extend parallel to each other along most of the interior volume of the mattress 50 and their longitudinal edges are electronically or ultrasonically sealed to the top and bottom walls 51 and 52 providing such gussets as means for maintaining a suitable slab-like shape for the water filled envelope defining the main body of the assembly 50.

Further modifications to the mattress and transducer mounting structures shown in the drawings include the following:

I. In the embodiment shown in FIG. 2, the transducer assembly 30 may be supported by the top or bottom wall of the inflatable mattress and may be located at either end thereof or disposed against or within one of the tubular formations 17 of the mattress. For example, such transducer assembly may be secured to a portion of one of the tubular formations 17 which extend along either edge of the mattress and so located that the cable extending to the transducer assembly is not compressed by the mattress when a person is lying on the mattress. Conversely, the flexible cable 44 may extend partly through the interior of the mattress, may be taped or sealed in a pocket to the exterior of the mattress to an end or edge thereof or may be secured to a coupling which plugs into a coupling or connector portion of the transducer assembly 30.

II. While the transducer assembly of FIGS. 2–4 is shown partially extending into the interior of the mattress through a fitting sealed to the wall of the mattress through an opening therein, it may also be connected or connectable to a fitting sealed to the exterior of the wall of the mattress and acoustically coupled to the liquid within the mattress through either the flexible material of the mattress wall or a coupling disc or device which is sealed to said wall or across an opening therein.

III. A plurality of similar or different transducers may be secured to the mattresses illustrated in the drawings or modifications thereof as described for sensing the same or different variables. For example, a plurality of sound detection transducers may be so connected or acoustically coupled to either or both the top and bottom walls of the mattress for detecting different body sounds such as heart beat, respiration rate and other cardiographic sounds. A temperature sensing transducer may also be similarly mounted or otherwise disposed on or within the mattress to sense body temperature of the person resting or reclining thereon. The sensor, for example, may be secured or sealed to the outer surface of the top wall 13 for contact with the body or head of the patient and may be connected by thin wires or flat conducting strips sealed in flexible plastic and sealed or taped to the flexible top wall of the mattress extending to an edge located female or pluggable male connector to which a flexible wire may extend from a source of power and instrumentation or transmitting means. Such transducer may also be connected to a flat chip mounted microminiature short wave transmitter and a flat battery for powering same to transmit the results of temperature sensing to a local short wave receiver located within the room in which the mattress is used and connected to insturmentation and retransmission means. The transducer, battery and transmitter may be provided in a flat container which is taped, sealed or otherwise secured to the top wall of the mattress at a convenient location to permit it to sense temperature(s) of the person lying on the mattress, and to generate and short wave transmit signals indicative of such temperatures together with signals indicative of other physiological variables sensed as described to a local receiver. In such an arrangement, one or more of the described body vibration sensors disposed within or against the wall of the mattress or located in the same package as the temperature sensor may also have its signals representing body vibrations or noise transmitted via the same short wave transmitter to said short wave receiver for analysis, monitoring and retransmission to instrumentation located remote from the room in which the patient is resting or sleeping.

Monitoring of the signals generated or modulated by the sensor or transducer 38 or any of the other described transducers, is effected by conventional means including a receiver for such signals which is connected to the conductors of the cable 44 or adapted to receive the described short wave signals and as set forth in my copending patent application entitled "physiological Parameter Sensing and Warning System" filed on or about Aug. 6, 1979 wherein the received signals are electronically processed and employed to operate a display or alarm and, in certain instances, are retransmitted either in the form they are receiver or after being digitized or processed to provide digital indications thereof such as codes.

Monitoring of the signals generated by the described sensor(s) may also be effected by means of a display or alarm secured either to the mattress wall adjaent to or as part of the housing containing the transducer or within a housing connected to cable 44 and located adjacent the mattress. Such housing may also contain microprocessing electronic means for processing the signals so generated to dtermine the condition of the patient and operable to generate output control signals for controlling the alarm and display means as provided in said copending application or otherwise disclosed in the prior art.

I claim:

1. An apparatus for detecting body vibrations such as caused by heartbeats and the like comprising:
    first means for sensing sounds and transducing the sounds sensed to electrical signals,
    second means including a container for a liquid having a flexible top wall on which a person may recline,
    a liquid sound transmitting medium contained within said container to provide the body of a person disposed against said flexible top wall in sound coupling relation with said first means,
    means for supporting said first means in sound coupling relation with the liquid in said container to permit said transducing means to pick up body sounds of a person reclining on said flexible top wall, which body sounds are transmitted from the body of said person through said flexible top wall of said container and through the liquid in the container to said first means,
    sound transmission means connected to said first means for transmitting signals generated by sounds sensed thereby, receiving means for receiving the signals generated by said first means and transmitted thereto by said transmission means, and
    indicating means connected to said receiving means for indicating body sounds generated within the body of a person reclining on said flexible top wall of said container and transmitted through said sound transmission medium within said container.

2. An apparatus in accordance with claim 1 wherein at least a portion of said first means protrudes into the liquid in said container and is contacted by said liquid.

3. An apparatus in accordance with claim 1 wherein said container is made substantially of flexible sheet material forming a flexible bag-like enclosure and contains sufficient liquid to permit said liquid to contact all of the interior walls of the container so that body vibrations imparted to the top wall on which the patient is reclining will be transmitted through said flexible top wall to said liquid.

4. An apparatus in accordance with claim 3 wherein said first means includes a housing and a flange circumscribing said housing, said housing extending through an opening in said flexible sheet material with said flange sealed across said opening to flexible sheet material surrounding said opening.

5. An apparatus in accordance with claim 3 including a flexible cable connected to said sound sensing means and extending beyond said container and defining said transmission means.

6. An apparatus in accordance with claim 5 wherein said first means includes a housing supporting said sound sensing means, said sound sensing means housing being supported by the bottom wall of said flexible container.

7. An apparatus in accordance with claim 3 wherein said container is in the shape of a substantially flat mattress having a plurality of elongated tubular formations formed of said flexible sheet material and extending most of the length of said container.

8. An apparatus in accordance with claim 1 wherein said sound sensing means is supported by the bottom wall of said container.

9. An apparatus in accordance with claim 8 wherein said sound sensing means is supported within a housing which is sealed to a portion of the wall of said container and extends through an opening in said container wall.

10. An apparatus in accordance with claim 1 wherein said container has a bottom wall portion and said first means comprises a sound-to-electrical energy transducer supported by said bottom wall of said container in sound coupling relation with the liquid in said container so as to permit said transducer to receive body sounds transmitted through the top wall of the container and liquid therein from the body of a person disposed against the top wall of the container.

* * * * *